United States Patent [19]

Heldebrant

[11] Patent Number: 5,061,484

[45] Date of Patent: Oct. 29, 1991

[54] PERFLUOROCHEMICAL EMULSION WITH STABILIZED VESICLES

[75] Inventor: Charles M. Heldebrant, Arcadia, Calif.

[73] Assignee: Alpha Therapeutic Corporation, Los Angeles, Calif.

[21] Appl. No.: 321,755

[22] Filed: Mar. 10, 1989

Related U.S. Application Data

[63] Continuation-in-part of Ser. No. 166,690, Mar. 11, 1988, abandoned.

[51] Int. Cl.$^5$ .................... A61K 31/74; A61K 31/02; A61K 31/025; A01N 29/04
[52] U.S. Cl. .................... 424/78; 514/672; 514/743; 514/756; 514/832
[58] Field of Search ............... 514/315, 672, 789, 776, 514/944, 743, 756, 832; 424/78; 544/351

[56] References Cited

U.S. PATENT DOCUMENTS

| | | | |
|---|---|---|---|
| 3,962,439 | 6/1976 | Yokoyama et al. | 424/248 |
| 4,252,827 | 2/1981 | Yokoyama et al. | 424/366 |
| 4,285,928 | 8/1981 | Wada et al. | 424/5 |
| 4,397,870 | 8/1983 | Sloviter | 424/325 |
| 4,423,077 | 12/1983 | Sloviter | 424/325 |
| 4,425,347 | 1/1984 | Yokoyama et al. | 424/256 |
| 4,443,480 | 4/1984 | Clark, Jr. | 424/352 |
| 4,497,829 | 2/1985 | Sloviter | 514/672 |
| 4,569,784 | 2/1986 | Moore | 252/315 |
| 4,596,810 | 6/1986 | Yokoyama et al. | 514/306 |
| 4,814,446 | 3/1989 | Erner | 544/351 |

OTHER PUBLICATIONS

D. S. Johnston et al, "Phospholipid Polymers—Syntyhesis and Spectral Characteristics," Biochimica et Biophysica Acta, 602 (1980), 57–69.
S. L. Regen et al, "Polymerized Phosphatidylcholine Vesicles, Synthesis and Characterization," Journal of the American Chemical Society, 1982, vol. 104, 791–795.
R. L. Juliano et al, "Interactions of Polymerized Phospholipid Vesicles with Cells, Uptake, Processing and Toxicity in Macrophages," Biochimica et Biophysica Acta, 812 (1985), 42–48.
S. L. Regen et al, "Polymerized Vesicles," Journal of the American Chemical Society, 1980, vol. 102, 6638–6640.
A. Akimoto et al, "Polymer Model Membranes," Angew. Chem. Int. Ed. Engl., 20 (1981) vol. 1, 90–91.
F. Bonte et al, "Interactions of Polymerizable Phosphatidylcholine Vesicles with Blood Components: Relevance to Biocompatibility," Biochimica et Biophysica Acta, 900 (1987), 1–9.
S. L. Regen, "Polymerized Phosphatidylcoline Vesicles as Drug Carriers," Annals of the New York Academy of Sciences, vol. 446 (1985) 296–307.
Hans-Henning Hub et al, "Polymerizable Phospholipid Analogues—New Stable Biomembrane and Cell Models," Angew, Chem. Int. Ed. Engl., 19 (1980) No. 11, 938–940.
L. Gros et al, "Polymeric Antitumor Agents on a Molecular and on a Cellular Level?," Angew. Chem. Int. Ed. Engl., 20, (1981), 305–325.
H. Ohno, "Polymerized Liposomes as a Stable Carrier for Synthetic Hemes or Hemoqlobin," Blood Substitutes, (1989) 631–632.
E. Hasegawa et al, "Interaction of Oxygen Carrying Microparticles with Blood Components and Clearance from Blood Stream," Blood Substitutes, (1989) 673–674.

Primary Examiner—Thurman K. Page
Assistant Examiner—Carlos Azpuru
Attorney, Agent, or Firm—Christie, Parker & Hale

[57] ABSTRACT

A stable perfluorochemical emulsion is provided which comprises perfluorochemical particles in stabilized vesicles. The vesicles comprise a biocompatible polymer formed by coating the perfluorochemical particles with one or more phospholipid monomer(s) and polymerizing the monomer(s).

38 Claims, No Drawings

PERFLUOROCHEMICAL EMULSION WITH STABILIZED VESICLES

RELATED APPLICATIONS

This application is a continuatio-in-part of U.S. Application Ser. No. 07/166,690 filed Mar. 11, 1988 and now abandoned, which is incorporated herein by this reference.

FIELD OF THE INVENTION

The present invention relates to stable perfluorochemical emulsions and to the emulsification techniques and ingredients used int heir preparation.

BACKGROUND OF THE INVENTION

Because perfluorochemicals have the ability to releasably bind oxygen, perfluorochemical preparations have been evaluated for use as blood substitutes and as ischemic modifiers. Such perfluorochemical preparations are typically prepared by emulsifying the perfluorochemical compound in an aqueous medium to form a perfluorochemical emulsion. Perfluorochemical emulsions are free of infectious agents and antigens, and their use obviates the need for blood typing of the recipient.

Although perfluorochemicals are chemically inert, they appear to adversely affect blood platelets and clotting factors. This adverse effect is believed to be due to the low surface tension of perfluorochemicals.

In an effort to avoid the adverse effect of perfluorochemicals on blood platelets and clotting factors, perfluorochemical emulsion particles are coated with a lipid, such as lecithin Emulsions containing lipid-coated perfluorochemical particles are, for example, disclosed in U.S. Pat. Nos. 3,962,439, 4,252,827, 4,423,077 and 4,497,829.

The prior-art perfluorochemical emulsions do not have a sufficiently high level of stability to withstand sterilization at elevated temperatures followed by storage in the liquid state at room temperature. Thus, their storage life in an unfrozen state is shorter than desired.

SUMMARY OF THE INVENTION

A perfluorochemical emulsion of enhanced stability is therefore provided in accordance with this invention to overcome the problems associated with high temperature sterilization and short shelf life. The emulsion comprises perfluorochemical particles contained within stabilized vesicles which are formed of a biocompatible polymer.

In a preferred embodiment, the method for producing the perfluorochemical emulsions of this invention includes the step of combining a perfluorochemical and a monomeric emulsifying material in the absence of a polymerization initiator to form a mixture. Preferably, the monomeric emulsifying material is a phospholipid monomer wherein each of the acyl chains of the phospholipid comprises a fatty acid moiety selected independently from the group consisting of conjugated di-ene fatty acids, conjugated di-yne fatty acids, conjugated ene-yne fatty acids, and fatty acids containing sulphydryl groups.

The perfluorochemical material and monomeric-emulsifying agent are homogenized in an aqueous medium until perfluorochemical particles of a desired size are coated with the monomeric emulsifying material forming an emulsion. Preferably, the diameter of the perfluorochemical particles (including their emulsifier coatings) is less than about 0.3 micron. The emulsion is exposed to an appropriate polymerization initiator which causes polymerization of the emulsifying material coating on the perfluorochemical particles. Such polymerization results in the formation of stabilized polymer vesicles which encapsulate or contain the perfluorochemical particles.

In a preferred embodiment, the phospholipid monomer is selected from the group consisting of phosphatidyl-L-cholines, phosphatidyl-L-serines, phosphatidyl-L-ethanolamines, and mixtures thereof. The preferred perfluorochemical is selected from the group consisting of perfluorodecalin, perfluorotertiary-amines, isoquinolidine perfluorochemical derivatives, and mixtures thereof.

DETAILED DESCRIPTION OF THE INVENTION

A stable aqueous perfluorochemical emulsion is provided in accordance with practice of principles of this invention. The particles of the emulsion comprise one or more perfluorochemical compounds contained-within stabilized vesicles which are formed of a biocompatible polymer.

The stable emulsions provided in accordance with this invention can be used as a medium for carrying oxygen to the tissues of a human; for example, they can be administered as a blood substitute or as an ischemic modifier. Because the perfluorocarbon particles are contained within polymerized (stabilized) vesicles, the emulsion is more stable than emulsions which incorporate perfluorochemical particles coated with a non-polymerized emulsifier coating. For example, the emulsions of this invention (1) can withstand higher and longer sterilization temperatures and times; (2) possess greater stability after sterilization which permits longer storage times; and (3) have longer circulating in vivo half-lives compared to emulsions of the same perfluorochemicals which incorporate non-polymerized emulsifier coatings.

In a preferred embodiment, the method for producing the perfluorochemical emulsions of this invention includes the steps of (1) combining a perfluorochemical and a monomeric emulsifying material in the absence of polymerization initiators to form a mixture; (2) homogenizing the mixture in an aqueous medium until perfluorochemical particles of a desired size are coated with the monomeric emulsifying material thereby forming a first emulsion; and (3) exposing the first emulsion to an appropriate polymerization initiator, for example, to ultraviolet radiation. Exposure to the polymerization initiator causes polymerization of the emulsifying material coating on the perfluorochemical particles to provide polymer vesicles which encapsulate or contain the perfluorochemical particles. The polymer vesicles are substantially more stable than non-polymerized lipid coatings on the perfluorochemical particles of standard prior-art emulsions The monomeric emulsifying materials useful in practice of this invention are those (1) which are effective to emulsify the particular perfluorochemical (or mixture of perfluorochemicals) beingused resulting in perfluorochemical particles having a diameter of less than about 0.3 micron coated with the emulsifying material and (2) which, after polymerization, provide stabilized perfluorocarbon polymer vesicles which are biocompatible when administered to a human in a physiologically acceptable emulsion medium. The term "biocompatible" as used herein means a lack of toxic interactions when administered to an animal or human.

Although any material which provides for the appropriate emulsification of the perfluorochemical material being used and which can be polymerized to form a biocompatible vesicle, is useful in practice of the present invention, it is preferred that the monomeric material be a monomeric lipid; preferably, a monomeric phospholipid. Most preferably, the monomeric lipid is photopolymerizable, i.e., it is polymerized by means of ultraviolet radiation. The phospholipids useful in practice of the present invention incorporate acyl chains which comprise a fatty acid moiety selected independently from the group consisting of conjugated di-ene fatty acids, conjugated di-yne fatty acids, conjugated ene-yne fatty acids, and fatty acids containing sulphydryl groups. Preferably, both fatty acid moieties of each phospholipid incorporate the same degree of unsaturation, i.e., they both contain conjugated di-ene bonds, or they both contain conjugated di-yne bonds, or they both contain ene-yne bonds. Preferably, the conjugated bonds are on the same carbons in both chains.

It is most preferred that the monomeric phospholipid cholines, be selected from the group consisting of phosphatidyl-L-phosphatidyl-L-serines, phosphatidyl-L-ethanolamines, and mixtures thereof. Preferably, the fatty acid moieties useful in the present invention are those which incorporate from about 10 to about 30 carbon atoms. Such useful acids are, for example, 2,4-octadecadienoic acid, 10,12-tricosadiynoic acid, 10,12-pentacosadiynoic acid, 12-methacryloyloxy dodecanoic acid, 1,2(lipoyl)dodecanoic acid, pentacosa-trans-10-ene,12-ynoic, and pentacosatrans-12-ene,10-ynoic acids.

Monomeric phospholipids useful in accordance with this invention may also be natural phospholipids which have been altered to render them polymerizable. Such alteration, for example, could involve chemical modification to remove some of the natural side chains, followed by chemical modification to place a desired side chain on the molecule followed by purification. The desired side chain would typically comprise a fatty acid having conjugated di-ene bonds, conjugated di-yne bonds, conjugated ene-yne bonds, or containing sulphydryl groups.

Non-limiting examples of monomeric phospholipids useful in practice of this invention incorporating di-ene fatty acid moieties include any of the 1,2-di-(X,X+2-dienoyl)-sn-glycero-3-phosphoryl-cholines, such as (1) 1,2-di-(2,4-octadecadienoyl)-sn-glycero-3-phosphorylcholine. Also useful are (2) Bis[12-(methacryloyloxy)-dodecanoyl]-L-α-phosphatidylcholine, (3) 1-[12-methacryloyloxy)dodecanoyl]-2-palmitoyl-L-α-phosphatidylcholine, and (4) 1-palmitoyl-2-[12-(methacryloyloxy)-dodecanoyl]-L-α-phosphatidylcholine. The 1,2-di-(2,4-octadecadienoyl)-sn-glycero-3-phosphoryl-choline material can be purchased from Nippon Oil and Fats Company Ltd., of Chiyoda-ku, Tokyo, Japan. Methods for synthesizing the phosphatidyl choline compounds Nos. (2), (3), and (4) are outlined in an article by S. L. Regen et al titled "Polymerized Phosphatidylcholine Vesicles. Synthesis and Characterization," Journal of the American Chemical Society, 1982, Vol. 104, pp. 791-795, which is incorporated herein by this reference. Other dieneoic acids useful in practice of the present invention are (5) 1,2-di(10,12-hexadecadieneoyl)-sn-glycero-3-phosphoryl choline. Materials for synthesizing the phosphatidyl choline compound No. (5) are outlined in B. Hupfer et al, Makromol. Chem, 1981, 182, p. 247, which is incorporated herein by this reference.

Non-limiting examples of monomeric phospholipids useful in practice of this invention comprising di-yne fatty acid moieties include any of the 1,2-di-(X,X+2-diynoyl)-sn-glycero-3-phosphoryl-choline acids or salts, such as (6) 1,2-di-(10,12-tricosadiynoyl)-sn-glycero-3-phosphoryl-choline and (7) 1,2-di-(10,12-pentacosadiynoyl)-sn-glycero-3-phosphoryl-choline. Methods for synthesizing the phosphatidyl choline compounds Nos. (6) and (7) are disclosed in an article by D. S. Johnston et al titled "Phospholipid Polymers—Synthesis and Spectral Characteristics," Biochimica and Biophysica Acta, 602 (1980) pp. 57-69, which is incorporated herein by this reference.

Non-limiting examples of monomeric phospholipids useful in practice of this invention comprising ene-yne fatty acid moieties include (8) 1,2-di-(tricosa-trans-10-ene-12-ynoyl or tricosa-trans-12-ene-10-ynoyl)-sn-glycero-3-phosphoryl-choline or (9) 1,2-di-(pentacosa-trans-10-ene-12-ynoyl or pentacosa-trans-12-ene-10-ynoyl)-sn-glycero3-phosphoryl-choline. Conjugated ene-yne fatty acids are made by reduction of one mole of the conjugated di-yne fatty acids with two moles of sodium in liquid ammonia. This leads to selective reduction of one of the two triple bonds to a double bond in the trans-configuration. The resulting product is then purified by vacuum distillation. The resulting acids will be a mixture of two isomers, for example, reduction of 10,12-pentacosadiynoic acid by sodium in liquid ammonia would yield pentacosa-trans-10-ene, 12-ynoic acid and pentacosa-trans-12-ene, 10-ynoic acid. These acids would be used without separation in the preparation of phosphatidyl-L-cholines by the methods disclosed in D. S. Johnston et al, Biochem. Biophys. Acta 602, (1980), pp. 57-69, which are described above as being useful for the preparation of di-yne derivatives of phosphatidyl-L-choline.

An example of a monomeric phospholipid useful in practice of this invention comprising fatty acid moieties incorporating sulphydryl groups is

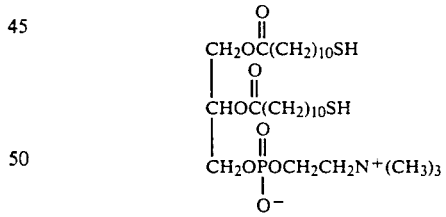

Methods for synthesizing the above-described sulphydryl-containing monomeric phospholipid, for example, is outlined in an article by S. Regen titled "Polymerized Phosphatidylcholine Vesicles as Drug Carriers," Annals of the New York Academy of Sciences, Vol. 446 (1985), pp. 296-307, which is incorporated herein by this reference.

The perfluorochemical compounds useful in preparing the emulsions of the present invention include, but are not limited to, those disclosed in U.S. Pat. Nos. 3,962,439, 4,252,827, 4,425,347 and 4,596,810, which are incorporated herein by this reference. Preferred perfluorochemical compounds include perfluorodecalin, perfluorotertiary-amines, such as perfluorotri-n-propylamine, and perfluorotri-n-butylamine, and isoquinolidine derivatives of perfluorochemicals. Perfluorodecalin is particularly preferred.

The emulsion particles useful in accordance with the present invention can comprise a single perfluorochemical or can comprise mixtures of perfluorochemicals. Preferred perfluorochemical mixtures include (1) perfluorodecalin and perfluorotri-n-propylamine; (2) perfluorotri-n-propylamine and perfluorotri-n-butylamine; (3) perfluoro-N,N'-dimethylcyclohexylmethyl-amine and perfluorodecalin; (4) perfluoro-3,3,1-trimethylbicyclo [3.3.1] nonane and perfluoro-N,N'-dimethylcyclohexylmethylamine; and (5) perfluorochemical isomeric mixtures, such as cis- and trans-perfluorodecalin.

Polymerization of the monomeric emulsifying material may be initiated in a number of ways, depending on the material. Examples of polymerization initiation stimulation include ultraviolet (UV) radiation, X-ray radiation, heat, and chemical initiation, for example, using azoisobutylnitrile (AIBN) or azobis-(2-amidinopropane) dihydrochloride (AAPD). Preferably, the monomeric phospholipids are photopolymerizable, i.e., they can be initiated by UV radiation.

In one embodiment, the stable emulsion of this invention is formed by providing a mixture of one or more monomeric phospholipids and one or more perfluorochemical materials in water so that the % w/v of the perfluorochemical material is preferably from about 10% to about 50%, more preferably from about 25% to about 35%, and the % w/v of the monomeric phospholipid is preferably from about 0.05% to about 5%, more preferably from about 1.5% to about 2.5%. The symbol "% w/v" as used herein means the amount of material by weight in grams based on 100 milliliters of the resulting emulsion. The mixture is held at approximately room temperature, and nitrogen or carbon dioxide gas is bubbled through the solution for 15 minutes to saturate the solution to remove oxygen. The presence of oxygen in the perfluorochemical/monomeric phospholipid mixture prior to homogenization tends to lead to an undesirably high level of free fluoride. Accordingly, it is preferred that oxygen be removed from the mixture prior to homogenization. The oxygen is typically removed by saturating the mixture, as described above, with nitrogen or carbon dioxide gas.

After the oxygen is removed from the mixture, the mixture is homogenized with a high shear mixture, such as a Turbo-mixer under a blanket of inert gas to produce a crude emulsion. The average particle size of the crude emulsion is measured by inelastic laser light scattering, using, for example, a Brookhaven BI-90 instrument, provided by Brookhaven Instruments Co., of Holtsville, N.Y. 11742. Typically, the average particle size of the crude emulsion is greater than about 1-2 microns. The crude emulsion is then passed through a Manton-Gaulin homogenizer, or similar high-pressure homogenizer, a sufficient number of times so that the final particle size is less than a selected value, for example, less than about 0.3 micron. Emulsification is done under a nitrogen stream at pressures 200–600 kg/cm$^2$ at temperatures of from about 4° C. to about 80° C., preferably from about 40° C. to about 50° C. During homogenization in the Manton-Gaulin homogenizer, the particle size of a sample taken at the end of each pass is measured. When the average particle size reaches a plateau value, usually between 0.05 and 0.16 micron, typically after 6 or 7 homogenization steps, the emulsification is complete.

The perfluorochemical particles (including the coating of polymerizable monomeric phospholipid) preferably have a diameter less than about 0.3 micron, more preferably are in the range of from about 0.1 to about 0.3 micron, and most preferably are from about 0.15 to about 0.2 micron.

Perfluorochemical particles larger than about 0.3 micron in diameter are not desired because such particles tend to be more toxic than smaller particles and are removed relatively rapidly from the circulation by the reticuloendothelial system (RES). Although emulsion particles smaller than about 0.1 micron in diameter can be prepared, such particles are difficult to prepare using current emulsification and sterilization technology and, hence, are not preferred. Particles prepared with phospholipid monomers and the example perfluorochemicals typically have a mean size of from about 0.1 to about 0.2 micron.

The final size of the emulsion particles is a function of the perfluorochemical or perfluorochemicals used, the monomeric phospholipid emulsifier, and the energy imparted to the emulsion during the emulsification process. For example, emulsions made with perfluorotri-n-butylamine have smaller particle sizes than emulsions made with perfluorodecalin, perfluorotri-n-propylamine or combinations thereof. Although emulsifiers such as Pluronic F-68, a non-ionic surfactant produced by BASF-Wyandotte, Inc., of Wyandotte, Mich., can be used in addition to the above-described polymerizable (monomeric) phospholipid emulsifiers, it is preferred that the monomeric phospholipid emulsifiers be used alone. Using only polymerizable (monomeric) emulsifiers results in a polymerized vesicle which is made up in its entirety of a polymerized material; whereas, when a nonpolymerizable emulsifier is used in conjunction with the monomeric phospholipid, portions of the vesicle which encapsulate the perfluorochemical will be unpolymerized. This results in less stable emulsions.

The stabilized emulsions provided in accordance with this invention may be isotonic, containing an appropriate amount of sodium chloride or other electrolytes, including the components in the Ringers solution or lactated Ringers solution. For that purpose, the presence of glycerine in an amount of 2.5% (w/v) can be used because glycerine contributes to the stability, in addition to the isotonicity of the emulsions.

The stabilized perfluorochemical emulsions provided in accordance with practice of the present invention contain very finely divided perfluorocarbon particles encapsulated within stabilized polymeric vesicles. Thus, the particles do not aggregate into coarse particles during storage of the emulsions for a considerably long time. The emulsions can be administered to mammals without harm of tissue due to aggregation.

The stabilized perfluorochemical emulsions of the present invention can, for example, (1) be administered intravenously to animals or humans who are in need of blood; (2) be administered for treating metastasis or cancerous tumors; (3) be administered to oxygenate tumors to enhance the effect of radiotherapy; and (4) be administered to oxygenate tissue downstream from the catheter during angioplasty procedures.

The present invention is illustrated in greater detail by the following examples which should not be construed to limit the invention in any way.

EXAMPLE 1

Preparation of Perfluorochemical Emulsion Using the Polymerizable Monomeric Emulsifier 1,2-di-(10,12-tricosadivnoyl)-sn-glycero-3-phosphoryl-choline.

17.5 gm of perfluorodecalin and 7.5 gm of perfluorotrin-n-propylamine (17.5% w/v and 7.5% w/v, respectively) are mixed together in an aqueous medium with 2.0% w/v 1,2-di(10,12-tricosadiynoyl)-sn-glycero-3-phosphoryl-choline. The mixture is held at approximately room temperature and nitrogen gas is bubbled through the solution for 15 minutes to saturate the solution and remove oxygen. The mixture is crudely homogenized with a high shear Turbo-mixer under a blanket of inert gas (nitrogen) in the absence of UV light to provide perfluorochemical particles (perfluorodecalin/-perfluorotri-n-propylamine particles) coated with the 1,2-di-(10,12-tricosadiynoyl)-sn-glycero-3-phosphoryl-choline emulsifier. The size of the emulsion particles is measured using a Brookhaven BI-90 instrument and is found to be greater than about 1 micron in diameter. The crude emulsion is then passed through a Manton-Gaulin homogenizer under a nitrogen stream at a pressure of 200 to 600 kg/cm$^2$ at about 35°–45° C. and collected.

The particle size distribution of the emulsion is measured after each pass through the homogenizer, and is from about 0.1 to about 0.15 micron in diameter after 7 passes. The resulting emulsion is cooled to below the fluid-gel transition temperature of the monomeric phospholipid. The transition temperature of 1,2-di-(10,12-tricosadiynoyl)-sn-glycero-3-phosphoryl-choline is about 38° C. The 1,2-di-(10,12-tricosadiynoyl)-sn-glycero-3-phosphorylcholine coating is then polymerized by exposure of the emulsion to 254 nm UV light, provided by an R-52 Mineralight, which has a peak radiation emission of 254 nm and an energy output of approximately 1200 microwatts/cm$^2$ at 15 centimeters from the face for at least 30 minutes. The change in the degree of polymerization is seen by the color change in the emulsion or by UV spectral analysis of a sample of the emulsion. After the monomeric coating is polymerized, the emulsion is filtered through a 3-micron filter and placed in a glass vial. The vial is then flushed with nitrogen and sealed. The vial is autoclaved at 121° C. for 8 minutes and is cooled to room temperature. The resulting sterilized emulsion containing perfluorochemical particles encapsulated in vesicles ofpoly-1,2-di-(10,12-tricosadiynoyl)-sn-glycero-3-phosphoryl-choline is tested for particle size distribution, oxygen capacity, and toxicity.

To test the emulsion for oxygen capacity, a 0.5 ml or 1 ml sample of the non-oxygenated emulsion is taken and analyzed for carbon dioxide, oxygen, and nitrogen content by the method of Van Slyke. (D. D. Van Slyke and W. C. Stadie, The Determination of the Gases of the Blood, J. Biol. Chem., 59(1), 192, 1–42; D. D. Van Slyke and J. M. Neill, The Determination of Gases in Blood and Other Solutions by Vacuum Extraction and Monometric Measurement I, J. Biol. Chem., 61(2), 1921, 523–573. The two articles by Van Slyke et al are incorporated herein by this reference.) Oxygen is bubbled through the emulsion for 15 minutes at a flow rate of 2-3 liters per minute. A 0.5 ml or 1 ml sample of the resulting oxygenated emulsion is taken, and once again is analyzed for carbon dioxide, oxygen, and nitrogen content by the method of Van Slyke. The oxygen gas content after oxygenation less the oxygen gas content before oxygenation is the net oxygen capacity of the emulsion. This value is between 4 and 7 vol % oxygen at 760 mmHg pressure for a 25% w/v perfluorochemical emulsion. Alternatively, the samples may be analyzed for oxygen content in the Lexington Lex-O$_2$-Con oxygen apparatus (Lexington Instruments, Waltham, Mass.). A 20 microliter sample would be injected into the machine, the oxygen content before and after oxygenation determined, and the oxygen capacity calculated by difference. These or other methods will all give comparable results for oxygen capacity The 25% emulsion is diluted to 20% w/v by the addition of one-fifth volume of 4% sodium chloride solution. The resulting emulsion will be injected intravenously via the tail veins of Wistar rats at a rate of 1 ml/minute. Groups of 5–10 animals are given doses of 144, 72, 36, or 18 ml of emulsion/kg body weight. The animals are observed for acute toxic signs and symptoms, and for body weight gain and survival after seven days of observation. Animals are given food and water ad libitum. The emulsion is nontoxic if the LD$_{50}$, lethal dose for 50% of the animals, is greater than about 50 ml/kg.

EXAMPLE 2

Preparation of Perfluorochemical Emulsion Using the Polymerizable Monomeric Emulsifier 1,2-di-(10,12-pentacosadivnoyl)-sn-glycero-3-phosphoryl-choline.

The same procedure that is used for preparing and testing the emulsion of Example 1 is used for Example 2, except that (a) 1,2-di-(10,12-pentacosadiynoyl)-sn-glycero-3-phosphoryl-choline is used in place of 1,2-di-(10,12-tricosadiynoyl)-sn-glycero-3-phosphoryl-choline and (b) the resulting emulsion is cooled to below the fluid-gel transition temperature of 1,2-di-(10,12-pentacosadiynoyl)-sn-glycero-3-phosphoryl-choline, which is about 48° C.

EXAMPLE 3

Preparation of Perfluorochemical Emulsion Using the Polymerizable Monomeric Emulsifier 1,2-di-(2,4-octadecadienoyl)-sn-glycero-3-phosphorvl-choline.

17.5 gm of perfluorodecalin and 7.5 gm of perfluorotrin-propylamine (17.5% w/v and 7.5% w/v, respectively) are mixed together in an aqueous medium with 2.0% w/v 1,2-di(2,4-octadecadienoyl)-sn-glycero-3-phosphoryl-choline. The mixture is held at approximately room temperature, and carbon dioxide gas is bubbled through the solution for 15 minutes to saturate the solution and to remove oxygen. The mixture is crudely homogenized with a high shear Turbomixer under a blanket of carbon dioxide in the absence of polymerization initiators. The size of the emulsion particles is measured using a Brookhaven BI-90 instrument and is found to be greater than about 1-2 microns in diameter. The crude emulsion is then passed through a Manton-Gaulin homogenizer or similar high-pressure homogenizer and collected.

The particle size distribution is measured after each pass through the homogenizer and is about 0.15 micron after 7passes. The 1,2-di-(2,4-octadecadienoyl)-sn-glycero-3-phosphoryl-choline coating is then polymerized by adding 5 mol % (relative to the phospholipid concentration) of either Azoisobutylnitrile (AIBN) or azobis-(2-amidinopropane) dihydrochloride (AAPD)

and heating the emulsion to 60° C. for about 30 minutes. The change in the degree of polymerization is seen by UV spectral analysis of a sample of the emulsion. After the monomeric coating is polymerized, the emulsion is filtered through a 3-micron filter and placed in a glass vial. The vial is then flushed with nitrogen and sealed. The vial is autoclaved at 121° C. for 8 minutes and is cooled to room temperature. Using the same procedures used in Example 1, the sterilized, polymerized emulsion is tested for particle size distribution and oxygen capacity. The emulsion is also tested by means well known in the art for residual AIBN or AAPD, as appropriate. If the levels are higher than desired, the AIBN or AAPD is removed by washing, or the like.

Such washing can be accomplished by suspending 100 ml of the resulting emulsion in 100 ml of 4% sodium chloride solution and mixed. The mixed solution is then centrifuged at 3,000×g for approximately 30 minutes. The supernatant is discarded, and a volume of fresh 4% sodium chloride equal to the volume of the supernatant (approximately 200 ml) is added. The precipitated emulsion particles are resuspended in the 4% sodium chloride, and the suspension is once again separated by centrifugation. The washed emulsion particles are suspended in 100 ml of water for injection.

EXAMPLE 4

Preparation of Stabilized Emulsion for Intravenous Injection as a Radiation Sensitizer 100 ml of the emulsion prepared in Examples 1,2 or 3 are diluted by the addition of 25 ml of 4% sodium chloride solution. The resulting solution is mixed. The emulsion is then administered to tumor-bearing rats at a dose of from about 8-12 ml/kg intravenously via the tail vein. The rats are then allowed to breathe oxygen for 30 minutes, prior to and during radiation treatment. The tumor growth delay or surviving tumor cell fraction is used to determine the radiation sensitization effect.

EXAMPLE 5

Preparation of Stabilized Emulsion for Use in Percutaneous Transluminal Coronary Angioplasty 30 ml of solution 1, comprising 3.5% w/v sodium bicarbonate USP, 0.56% w/v potassium chloride USP, in water for injection USP, and 70 ml of solution 2, comprising 4.29% w/v sodium chloride USP, 1.29% w/v dextrose USP, anhydrous, 0.305% w/v magnesium chloride-6H$_2$O USP, 0.254% w/v calcium chloride-2H$_2$O USP, in water for injection USP, are added to 400 ml of the emulsions prepared in Examples 1, 2, or 3. The solutions are added sequentially and separately, and the emulsion is mixed after each addition. The composition of the mixed emulsion ready for administration are 14.0 g/100 ml perfluorodecalin, 6.0 g/100 ml perfluorotri-n-propylamine, 0.60 g/100 ml sodium chloride USP, 1.6 g/100 ml polymerized phospholipids .21 g/100 ml sodium bicarbonate USP, 0.18 g/100 ml dextrose USP, anhydrous, 0.043 g/100 ml magnesium chloride-6H$_2$O USP, 0.036 g/100 ml calcium chloride-2H$_2$O USP, 0.034 mg/100 ml potassium chloride USP, in water for injection USP.

EXAMPLE 6

Intravenous Injection of the Stabilized Perfluorochemical Emulsion as an Erythrocyte Substitute 30 ml of annex solution C, comprising 3.5% w/v sodium bicarbonate USP, 0.56% w/v potassium chloride USP, in water for injection USP, and 70 ml of annex solution H, comprising 4.29% w/v sodium chloride USP, 3.0 % w/v hydroxylethyl starch, 1.29% w/v dextrose USP, anhydrous, 0.305% w/v magnesium chloride-6H$_2$O USP, 0.254% w/v calcium chloride-2H$_2$O USP, in water for injection USP, are added to 400 ml of the emulsions prepared in Examples 1, 2, or 3. The solutions are added sequentially and separately, and the emulsion is mixed after each addition. The resulting emulsion is oxygenated by bubbling 1-2 liters per minute of oxygen through the mixed emulsion for 15-30 minutes. The resulting oxygenated emulsion is administered to a 150 gram conscious male Wistar rat. A double lumen catheter is placed in the right atrium of the rat heart under anesthesia. The rat is allowed to recover to full consciousness. The catheter is connected to a Harvard Infusion Pump (Harvard Apparatus, South Natick, Mass.) such that one side of the catheter infuses the oxygenated emulsion into the right atrium while the other catheter is withdrawing blood from the right atrium. The dose of emulsion is 24 ml. The animal is placed in a 100% oxygen atmosphere, and the exchange transfusion is carried out at a flow rate of 1 ml/minute until 24 ml of the emulsion is infused, and 24 ml of the blood-emulsion is removed from the rat. The resulting hematocrit of the rat after the transfusion is completed is 2-4%. The animal is allowed to breath 100% oxygen for day 1, 90% oxygen, 10% air for day 2, with the oxygen decreasing 10% and the air increasing 10% per day until day 7. The animal is then returned to room air. Animals exchanged with other non-oxygen-carrying materials to a hematocrit of 2-4% under these conditions will not survive. This test demonstrates the oxygen-carrying capacity of the emulsions of Examples 1, 2, and 3 in an in-vivo erythrocyte replacement test system.

The above descriptions of preferred embodiments of stable perfluorochemical emulsions and the emulsification techniques and ingredients used for their preparation are for illustrative purposes. Because of variations which will be apparent to those skilled in the art, the present invention is not intended to be limited to the particular embodiments described above. The scope of the invention is defined in the following claims.

What is claimed is:

1. A stable perfluorochemical emulsion comprising perfluorochemical particles contained within stabilized vesicles having a diameter of up to about 0.3 micron, the stabilized vesicles comprising a biocompatible polymer formed by coating the perfluorochemical particles with one or more phospholipid monomers and polymerizing the monomers.

2. A stable perfluorochemical emulsion as claimed in claim 1 wherein each of the acyl chains of such a phospholipid monomer comprises a fatty acid moiety selected independently from the group consisting of conjugated diene fatty acids, conjugated di-yne fatty acids, conjugated ene-yne fatty acids, and fatty acids containing sulphydryl groups.

3. A stable perfluorochemical emulsion as is claimed in claim 1 wherein such a phospholipid monomer is a photopolymerizable phospholipid monomer.

4. A stable perfluorochemical emulsion as is claimed in claim 1 wherein such a phospholipid monomer is selected from the group consisting of phosphatidyl-L-cholines, phosphatidyl-L-serines, phosphatidyl-L-ethanolamines, and mixtures thereof.

5. A stable perfluorochemical emulsion as is claimed in claim 1 in which such a phospholipid monomer is selected from the group consisting of phosphatidyl-L-choline, phosphatidyl-L-serine, phosphatidyl-L-ethanolamine, and mixtures thereof, wherein both acyl chains of each such phospholipid monomer incorporate a conjugated di-yne fatty acid moiety.

6. A stable perfluorochemical emulsion as is claimed in claim 5 in which such a phospholipid monomer is phosphatidyl-L-choline, wherein both acyl chains comprise conjugated di-yne fatty acid moieties with the conjugated di-yne bonds on the same carbons in both chains.

7. A stable perfluorochemical emulsion as is claimed in claim 5 in which such a phospholipid monomer is phosphatidyl-L-serine, wherein both acyl chains comprise diyne fatty acid moieties with the conjugated di-yne bonds on the same carbons in both chains.

8. A stable perfluorochemical emulsion as is claimed in claim 5 in which such a phospholipid monomer is phosphatidyl-L-ethanolamine, wherein both acyl chains comprise di-yne fatty acid moieties with the conjugated di-yne bonds on the same carbons in both chains.

9. A stable perfluorochemical emulsion as is claimed in claim 5 in which such a phospholipid monomer is phosphatidyl-L-choline, wherein both acyl chains comprise conjugated di-ene fatty acid moieties with the conjugated di-ene bonds on the same carbons in both chains.

10. A stable perfluorochemical emulsion as is claimed in claim 5 in which such a phospholipid monomer is phosphatidyl-L-serine, wherein both acyl chains comprise diene fatty acid moieties with the conjugated di-ene bonds on the same carbons in both chains.

11. A stable perfluorochemical emulsion as is claimed in claim 5 in which such a phospholipid monomer is phosphatidyl-L-ethanolamine, wherein both acyl chains comprise di-ene fatty acid moieties with the conjugated di-ene bonds on the same carbons in both chains.

12. A stable perfluorochemical emulsion as is claimed in claim 5 in which such a phospholipid monomer is phosphatidyl-L-choline, wherein both acyl chains comprise ene-yne fatty acid moieties with the conjugated ene-yne bonds on the same carbons in both chains.

13. A stable perfluorochemical emulsion as is claimed in claim 5 in which such a phospholipid monomer is phosphatidyl-L-serine, wherein both acyl chains comprise ene-yne fatty acid moieties with the conjugated ene-yne bonds on the same carbons in both chains.

14. A stable perfluorochemical emulsion as is claimed in claim 5 in which the phospholipid is phosphatidyl-L-ethanolamine, wherein both acyl chains comprise ene-yne fatty acid moieties with the conjugated ene-yne bonds on the same carbons in both chains.

15. A stable perfluorochemical emulsion as is claimed in claim 1 in which the perfluorochemical particle comprises a perfluorochemical selected from the group consisting of perfluorodecalin, perfluorotertiary-amine, andisoquinolidine perfluorochemical derivatives, and mixtures thereof.

16. A stable perfluorochemical emulsion as is claimed in claim 1 in which the perfluorochemical particle comprises a perfluorochemical selected from the group consisting of (a) perfluorodecalin and perfluorotri-n-propylamine; (b) perfluorotri-n-propylamine and perfluorotri-n-butylamine; (c) perfluoro-N,N'-dimethylcyclohexylmethylamine and perfluorodecalin; (d) perfluoro-3,3,1,-tri-methylbicyclo [3,3,1] nonane and perfluoro-N,N'-dimethylcyclohexylmethylamine; and (e) cis and trans perfluorodecalin.

17. A stable perfluorochemical emulsion as is claimed in claim 1 in which the polymeric vesicles have a diameter of about 0.15 to about 0.3 micron.

18. A stable perfluorochemical emulsion as is claimed in claim 17 in which the vesicles have a diameter of about 0.2 micron.

19. A stable perfluorochemical emulsion as is claimed in claim 1 in which the perfluorochemical particle comprises perfluorodecalin and perfluorotri-n-propylamine, and the phospholipid monomer is phosphatidyl-L-choline, wherein both acyl chains comprise conjugated di-yne fatty acid moieties with the conjugated di-yne bonds on the same carbons in both chains, and the polymeric vesicle diameter is from about 0.15 to about 0.3 micron.

20. A stable perfluorochemical emulsion in a physiologically acceptable aqueous medium comprising perflorochemical particles contained with stabilized vesicles having a diameter of up to about 0.3 micron. The stabilized vesicles comprising a biocompatible polymer formed by coating the perfluorochemical aprticles with a phospholipid monomer selected from the group consisting of phosphatidyl-L-cholines, phosphatidyl-L-serines, phosphatidyl-L-ethanolamines, and mixtures thereof, and polymerizing the monomers.

21. A stable perfluorochemical emulsion is claimed in claim 20 wherein both acyl chains of the phospholipid monomer comprise fatty acid moieties selected from the group of conjugated di-yne fatty acids, conjugated di-ene fatty acids, and conjugated ene-yne fatty acids, wherein the unsaturated bonds are on the same carbons in both acyl chains.

22. A method for producing a stable perfluorochemical emulsion, the method comprising the following steps:
 (a) combining a perfluorochemical and a phospholipid monomer in the absence of a polymerization initiator to form a mixture;
 (b) homogenizing the mixture in an aqueous medium to form an emulsion comprising perfluorochemical particles of less than about 0.3 micron in size coated with the phospholipid monomer; and
 (c) exposing the emulsion to a polymerization initiator to cause such phospholipid monomer coatings to polymerize to thereby form biocompatible phospholipid polymeric vesicles having a diameter of up to 0.3 micron, the emulsion comprising such stabilized phospholipid polymer vesicles containing the perfluorochemical particles.

23. The method of claim 22 further comprising removing oxygen from the perfluorochemical/phospholipid monomer mixture before the mixture is homogenized in the aqueous medium.

24. The method of claim 22 wherein the phospholipid monomer is a photopolymerizable phospholipid monomer.

25. The method of claim 22 wherein the phospholipid monomer comprises a fatty acid moiety selected independently from the group consisting of conjugated di-ene fatty acids, conjugated di-yne fatty acids, conjugated ene-yne fatty acids, fatty acids containing sulphydryl groups, and mixtures thereof.

26. The method of claim 22 wherein the phospholipid monomer is selected from the group consisting of phosphatidyl-L-cholines, phosphatidyl-L-serines, phosphatidyl-L-ethanolamines, and mixtures thereof.

27. The method of claim 22 wherein the phospholipid monomer is selected from the group consisting of phosphatidyl-L-choline, phosphatidyl-L-serine, phosphatidyl-L-ethanolamine, and mixtures thereof, and both acyl chains in each such phospholipid comprise a conjugated di-yne fatty acid moiety.

28. The method of claim 22 wherein the phospholipid is phosphatidyl-L-choline, and both acyl chains of the phosphatidyl-L-choline comprise conjugated di-yne fatty acid moieties with the conjugated di-yne bonds on the same carbons in both chains.

29. The method of claim 22 wherein the phospholipid is phosphatidyl-L-serine, and both acyl chains of the phosphatidyl-L-serine comprise di-yne fatty acid moieties with the conjugated di-yne bonds on the same carbons in both chains.

30. The method of claim 22 wherein the phospholipid is phosphatidyl-L-ethanolamine, and both acyl chains of the phosphatidyl-L-ethanolamine comprise di-yne fatty acid moieties with the conjugated di-yne bonds on the same carbons in both chains.

31. The method of claim 22 wherein the phospholipid is selected from the group consisting of phosphatidyl-L-choline, phosphatidyl-L-serine, phosphatidyl-L-ethanolamine, and mixtures thereof, and both acyl chains in each such phospholipid comprise a conjugated di-ene fatty acid moiety.

32. The method of claim 22 wherein the phospholipid is phosphatidyl-L-serine, and both acyl chains comprise di-ene fatty acid moieties with the conjugated di-ene bonds on the same carbons in both chains.

33. The method of claim 22 wherein the phospholipid is phosphatidyl-L-ethanolamine, and both acyl chains comprise di-ene fatty acid moieties with the conjugated di-ene bonds on the same carbons in both chains.

34. The method of claim 22 wherein the phospholipid is phosphatidyl-L-choline, and both acyl chains comprise conjugated ene-yne fatty acid moieties with the conjugated ene-yne bonds on the same carbons in both chains.

35. The method of claim 22 wherein the phospholipid is phosphatidyl-L-serine, and both acyl chains comprise ene-yne fatty acid moieties with the conjugated ene-yne bonds on the same carbons in both chains.

36. The method of claim 22 wherein the phospholipid is phosphatidyl-L-ethanolamine, and both acyl chains comprise ene-yne fatty acid moieties with the conjugated ene-yne bonds on the same carbons in both chains.

37. The method of claim 22 wherein the perfluorochemical is selected from the group consisting of perfluorodecalin, perfluorotertiary-amine, isoquinolidine perfluorochemical derivatives, and mixtures thereof.

38. The method of claim 37 wherein the perfluorochemical is a mixture of perfluorodecalin and perfluoro-tri-n-propylamine.

* * * * *